United States Patent
Banner et al.

(10) Patent No.: US 8,962,883 B2
(45) Date of Patent: Feb. 24, 2015

(54) LEVULINIC ACID FROM FUNGAL BIOMASS

(75) Inventors: Larry Todd Banner, Ottumwa, IA (US); John Andrew Bohlmann, Ottumwa, IA (US); Brian J. Brazeau, Excelsior, MN (US); Tzyy-Jan Han, Pella, IA (US); Paul Loucks, Blakesburg, IA (US); Shannon Nicole Shriver, Pella, IA (US); Shuang Zhou, Pella, IA (US)

(73) Assignee: Cargill, Incorporated, Wayzata, MN (US)

( * ) Notice: Subject to any disclaimer, the term of this patent is extended or adjusted under 35 U.S.C. 154(b) by 363 days.

(21) Appl. No.: 13/375,058

(22) PCT Filed: May 29, 2010

(86) PCT No.: PCT/US2010/036781
§ 371 (c)(1),
(2), (4) Date: Mar. 27, 2012

(87) PCT Pub. No.: WO2010/138957
PCT Pub. Date: Dec. 2, 2010

(65) Prior Publication Data
US 2012/0178967 A1    Jul. 12, 2012

Related U.S. Application Data

(60) Provisional application No. 61/217,376, filed on May 29, 2009.

(51) Int. Cl.
*C07C 59/185* (2006.01)
*B01D 3/10* (2006.01)
*C07C 51/44* (2006.01)

(52) U.S. Cl.
CPC ........................... *C07C 51/44* (2013.01)
USPC .............................. 562/577; 203/80

(58) Field of Classification Search
CPC ........................... C07C 59/185; C07D 309/14
See application file for complete search history.

(56) References Cited

U.S. PATENT DOCUMENTS

| | | | |
|---|---|---|---|
| 2,684,982 A | 7/1954 | Duntop | |
| 2,738,367 A | 3/1956 | Redmon | |
| 4,144,047 A | 3/1979 | Franz et al. | |
| 5,189,215 A | 2/1993 | Farnleitner et al. | |
| 5,859,263 A | 1/1999 | Ghorpade et al. | |
| 2002/0160459 A1 | 10/2002 | Berry et al. | |
| 2004/0077055 A1* | 4/2004 | Fosdick et al. | 435/85 |
| 2006/0172392 A1 | 8/2006 | Zhou et al. | |
| 2006/0217578 A1 | 9/2006 | Rao et al. | |

FOREIGN PATENT DOCUMENTS

GB 583533 * 12/1946
WO 98/19986 A1 5/1998

OTHER PUBLICATIONS

Aldrich, Aldrich Handbook of Fine Chemicals and Laboratory Equipment, 2002, Milwaukee, WI, p. 1124.*
"Levulinic Acid," The Merck Index, 14th Edition, ver. 14.3 2006, Knovel—Reliable and relevant technical reference, www.knovel.com, 1 page.

* cited by examiner

*Primary Examiner* — Paul A Zucker (57) ABSTRACT

Systems and methods for producing levulinic acid from fungal biomass are disclosed. In one implementation, a method for distilling levulinic acid from a glucosamine-containing feedstock is disclosed that yields a relatively pure (e.g., 90% or greater) levulinic acid product from an otherwise problematic waste stream.

17 Claims, 3 Drawing Sheets

LEVULINIC ACID FROM FUNGAL BIOMASS

CROSS-REFERENCE TO RELATED APPLICATIONS

This application claims the benefit of the PCT Patent Application, Serial No. PCT/US2010/036781, filed 29 May 2010, entitled LEVULINIC ACID FROM FUNGAL BIOMASS, which claims the benefit of the U.S. Provisional Patent Application Ser. No. 61/217,376, filed 29 May 2009, entitled LEVULINIC ACID FROM FUNGAL BIOMASS, which are hereby incorporated by reference in their entirety.

TECHNICAL FIELD

The present disclosure relates generally to production of levulinic acid. Aspects of the disclosure are particularly directed to separating levulinic acid from a glucosamine-containing feedstock.

BACKGROUND

Levulinic acid, also referred to as acetyl-propionic acid or 4-oxopentanoic acid, is known as a preservative and as an acidulant that is useful in carbonated and fruit juice beverages, jams, and jellies. It is also used as a starting product for a variety of organic chemicals, including plasticizers, solvents, and pharmaceutical compounds. For example, levulinic acid has been used to produce methyltetrahydrofuran, a fuel additive, and delta-amino levulinic acid, a broad-spectrum herbicide and pesticide.

Levulinic acid is commonly produced by reacting carbohydrates with mineral acids. Known starting materials for producing levulinic acid include molasses, fructose, food starches (e.g., tapioca meal or potatoes), and cellulosic materials such as wood, bagasse, or waste paper. The acid treatment typically yields an aqueous mixture containing levulinic acid, formic acid, and furfural, but being essentially free of glucosamine.

A variety of approaches have been proposed for separating levulinic acid from formic acid and furfural. For example, International Publication No. WO 98/19986 (Farone et al.) proposes separating levulinic acid from furfural and residual sulfuric acid by simulated moving bed chromatography. U.S. Pat. No. 5,859,263 (Ghorpade et al.) suggest preparing levulinic acid from corn starch and sulfuric acid via reactive extrusion. The levulinic acid in the resultant extrudate is removed by a filter press and steam distillation.

DETAILED DESCRIPTION

Overview

Specific details of several embodiments of the disclosure are described below with reference to FIGS. 1-3.

One aspect of the present disclosure is directed toward a method for producing levulinic acid. In accordance with this method, a glucosamine-containing feedstock is distilled in a first distillation at a first treatment temperature that is no greater than 110° C. to yield a first product fraction and a first distillate fraction. The glucosamine-containing feedstock comprises levulinic acid and at least 0.1 percent by weight (wt %) glucosamine. The levulinic acid concentration of the first product fraction is higher than the levulinic acid concentration of the glucosamine-containing feedstock. After the first distillation, the first product fraction is distilled in a second distillation at a second treatment temperature that is between 110° C. and 150° C. to yield a levulinic acid product and a residual product. The levulinic acid product contains at least 60 wt % levulinic acid.

Unless otherwise indicated, all numbers expressing quantities of ingredients, properties such as molecular weight, percentages, reaction conditions, and so forth used in the specification and claims are to be understood as being modified by the term "about." Accordingly, unless indicated to the contrary, the numerical parameters set forth are approximations that may depend upon the desired properties sought.

Method of Producing Levulinic Acid from Fungal Biomass

Aspects of the invention are particularly well suited for separating levulinic acid from a feedstock that contains glucosamine, e.g., glucosamine hydrochloride. In accordance with one implementation, the feedstock comprises an effluent stream, referred to herein as a mother liquor, from the production of glucosamine from a fungal biomass. Other glucosamine-containing feedstocks useful in other aspects of the invention may include, for example, effluent from the production of glucosamine from shellfish, as is known in the art.

Figure 1:
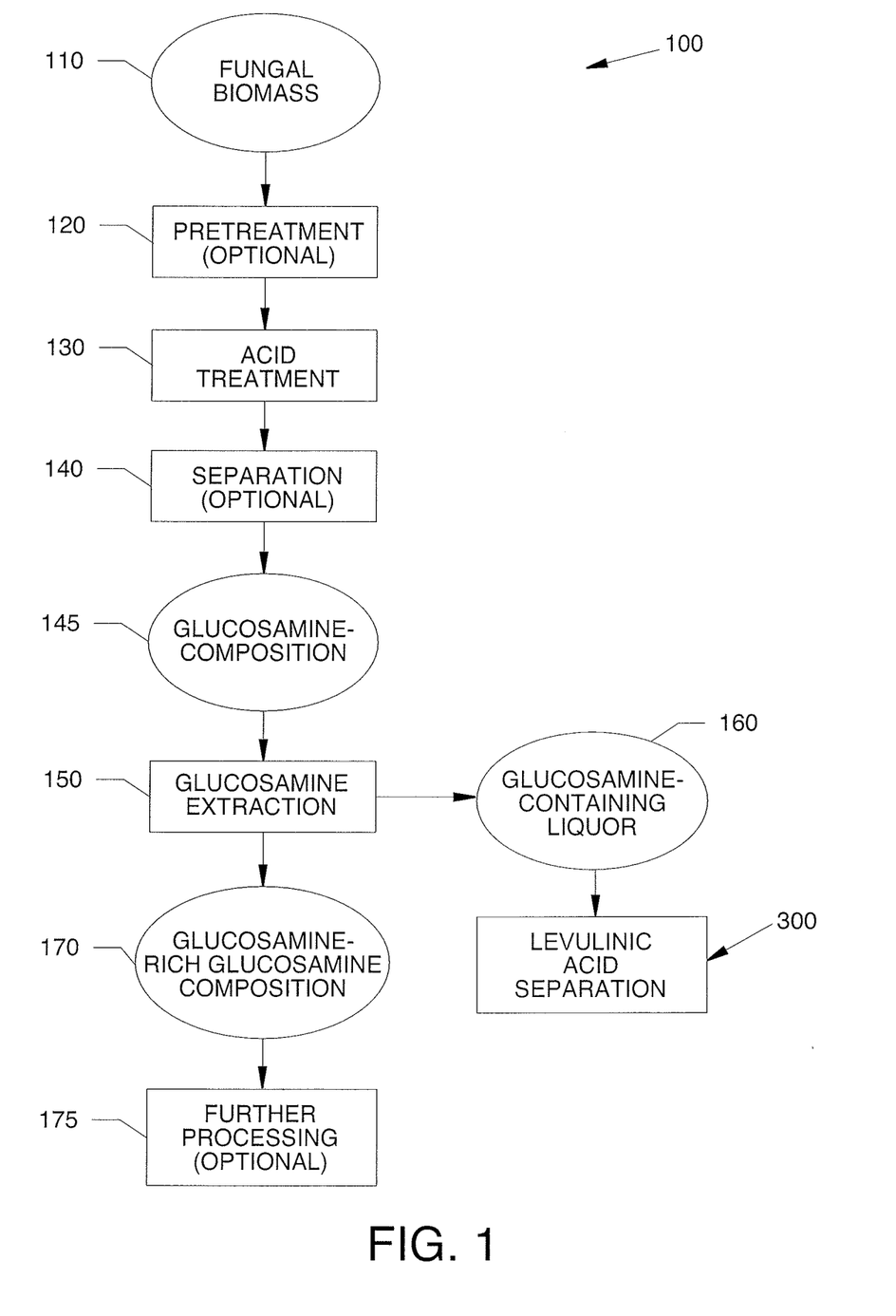
FIG. 1 is a flow diagram of one of the disclosed methods of producing levulinic acid.

FIG. 1 is a flow diagram schematically illustrating one useful fungal biomass treatment method 100 for producing a glucosamine product and a liquor that contains levulinic acid. This method 100 is outlined below, but aspects of the method 100, including aspects of the starting fungal biomass and a resultant glucosamine composition, are described in further detail in US Patent Application Publication No. US 2006/0172392, the entirety of which is incorporated herein by reference.

This method 100 includes providing a starting material that comprises a chitin-containing fungal biomass 110. This fungal biomass 110 may comprise a substantially uniform microbial fungal source, such as fungal sources derived from *Aspergillus* sp., *Penicillium* sp., *Mucor* sp., *Absidia* sp., *Actinomucor* sp., *Actostelium* sp., *Agaricus* sp., *Allomyces* sp. *Amylomyces* sp., *Copnnus* sp., *Cunninghamella* sp. *Didymium* sp., *Fusarium* sp. *Gongroneila* sp., *Lentinula* sp., *Mortierella* sp., *Mucorlopsis* sp., *Phycomyces* sp., *Rhizomucor* sp., and *Rhizopus* sp., and combinations thereof. Other useful sources of fungal biomass may include, without limitation, *Absidia ramosa*, *Gongronella butlerii*, *Mortierella spinosa*, *Mucor racemosus*, *Rhizopus nigricans*, *R. stolonifer*, *R. oryzae*, *A. nidulans*, *Thielavia terricola*, *Saccharomyces cerevisiae*, *Cheatomium lunasporium*, and combinations thereof. As used herein, "uniform fungal biomass" refers to fungal biomass comprising substantially the same species grown on substantially the same media, grown in a relatively controlled environment or other such conditions that lead to substantial uniformity in the biochemical make-up of the biomass. In other embodiments, however, the fungal biomass of step 110 is not uniform.

In some implementations of the method 100, the fungal biomass 110 is first treated in a pretreatment step 120 to remove some impurities and/or to improve glucosamine composition production. These treatments can include, for example, heating the biomass, adding digestive enzymes, mixing with an acid or base, mechanical agitation, ultrasonic cell disruption, or dewatering by compression. One such optional treatment for removing proteins, lipids, and residual citric acid involves pretreating the biomass in the presence of a base, such as 1-4% sodium hydroxide. Such a pretreatment step 120 is entirely optional, though, and many implementations do not employ a pretreatment step 120.

The fungal biomass 110 (whether pretreated or not) may then be subjected to an acid treatment step 130 in which the fungal biomass is reacted with a relatively aggressive acidic solution. Relatively strong (aggressive) acids may be used to hydrolyze the fungal biomass, including acids of concentrations less than 50 percent. Acids of concentrations of from 5 to 25 percent are also suitable.

In particular embodiments of the method 100, particular glucosamine compositions are formed by an aggressive acid treatment, reacting from 5 to 20 percent acid with from 2 to 50 percent pretreated biomass (based upon dry weight, although the biomass is typically processed with water present) and from 35 to 93 percent water. In certain implementations, the reaction mixture comprises from 8 to 12 percent hydrochloric acid, from 4 to 8 percent biomass (based upon dry weight), and from 80 to 90 percent water. In yet another embodiment, the acid solution is from 17 to 20 percent hydrochloric acid solution.

In the acid treatment step 130, the aggressive acid treatment mixture containing the biomass, acid, and water is heated and maintained at a relatively elevated temperature. The mixture is usually heated to a temperature at or near its boiling point (typically 90° C. to 106° C.) and maintained under reflux conditions for 5 hours or greater, more typically greater than 8 hours, and usually less than 16 hours. The reaction may continue long enough to have a complete breakdown of the chitin, but not so long as to be inefficient or to excessively decompose the glucosamine compositions.

Although reaction in the relatively aggressive acid solution produces a glucosamine composition, subsequent purification steps may be taken. The method 100 of FIG. 1 includes an optional separation step 140, which may comprise filtration, to remove particulate impurities, resulting in a substantially clear solution of the glucosamine composition 145. The solution contains an embodiment of glucosamine composition as well as small quantities of glucose and other components of the composition. The glucosamine composition 145 can be concentrated and some of the acid recovered can be recycled and reused.

The glucosamine composition 145 may include glucosamine in a variety of forms. For example, the glucosamine composition 145 may comprise one or more salts of glucosamine, including citrate, acetate, phosphate, sulfate, chloride, lactate, gluconate, etc. Also, the glucosamine in the glucosamine compositions can be substituted or modified without diverging from the scope of the invention. Thus, as used herein, the term glucosamine refers to the various forms of glucosamine, including salt complexes and substituted glucosamine. Likewise, the term glucosamine composition refers to compositions including glucosamine in such various forms.

The glucosamine composition 145 may then be subjected to a glucosamine extraction step 150 that yields a glucosamine-rich glucosamine composition 170 and a glucosamine-containing liquor 160. The extraction step 150 in one embodiment involves crystallizing the glucosamine, such as by adding ethanol to the concentrated solution or by continuing evaporation to the glucosamine composition solubility limit. The crystallized glucosamine can be separated from the remainder of the composition 145 by a separation process, such as filtration or centrifugation, leaving a majority of the crystallized glucosamine in the composition 170 and a minor portion of the glucosamine in the glucosamine-containing liquor 160.

The glucosamine-rich glucosamine composition 170 may be further processed in a further purification step 175. For example, the crystallized glucosamine that has been filtered out in the extraction step 150 may be dried and/or further treated to remove undesirable residual sugars. One method of removing such sugars is by dissolving the glucosamine composition in water and adding ethanol to again precipitate the glucosamine composition while undesirable sugars remain in solution. Alternatively, the solution can be treated by electrodialysis, chromatography, membrane filtration, or other suitable procedures to further increase the concentration of glucosamine in the glucosamine composition 170. The glucosamine composition 170 may optionally be decolorized and/or deodorized by, for example, treating the composition with ethanol, carbon, or other suitable material or method.

The composition of the glucosamine-containing liquor 160 will vary depending on the nature of the starting fungal biomass and the conditions in the optional pretreatment 120 (if any), the acid treatment step 130, the separation step 140 (if any) and the extraction step 150. The liquor 160 typically will include at least 3 percent by weight (wt %) glucosamine, e.g., 3-10 wt %, more commonly 4 wt % glucosamine or more, such as 4-8 wt %. In one commercially useful embodiment, the liquor 160 includes at least 5 wt % glucosamine, e.g., 5-7 wt %.

The liquor 160 also includes levulinic acid. The liquor 160 desirably includes at least 15 wt %, e.g., 15-40 wt %, levulinic acid, preferably at least 20 wt %, e.g., 20-35 wt %, levulinic acid. In some useful embodiments, the liquor includes 25-35 wt %, e.g., 25-30 wt %, levulinic acid.

The liquor 160 may also include varying amounts of other components. For example, the liquor may include a remaining quantity of the acid used in the acid treatment step 130. In one embodiment that uses hydrochloric acid in the acid treatment step, the liquor 160 includes 5-12 wt %, e.g., 7-12 wt %, hydrochloric acid, with typical concentrations of 7-10 wt % being expected to work well. In such an embodiment, at least a portion of the glucosamine in the liquor comprises a chloride salt of glucosamine, such as glucosamine hydrochloride. The liquor 160 produced in the process 100 of FIG. 1 may also include one or more of the following components:

| Component | Typical wt % in the liquor 160 |
| --- | --- |
| acetic acid | 0.25-3 wt %, e.g., 1-2 wt % |
| formic acid | less than 1 wt %, e.g., 0.1-0.7 wt % |
| hydromethyl furan (HMF) | 0-0.5 wt %, e.g., 0.01-0.2 wt % |
| Glucosamine degradates* | |

*Glucosamine degradates are byproducts of the degradation of glucosamine, e.g., by hydrolysis or thermal breakdown of the glucosamine.

As shown in FIG. 1, the glucosamine-containing liquor 160 may be delivered to a levulinic acid separation process 300 to yield a levulinic acid product from the liquor. One suitable levulinic acid separation process 300 is shown in more detail in FIG. 3 and discussed below.

System for Separating Levulinic Acid

Figure 2:
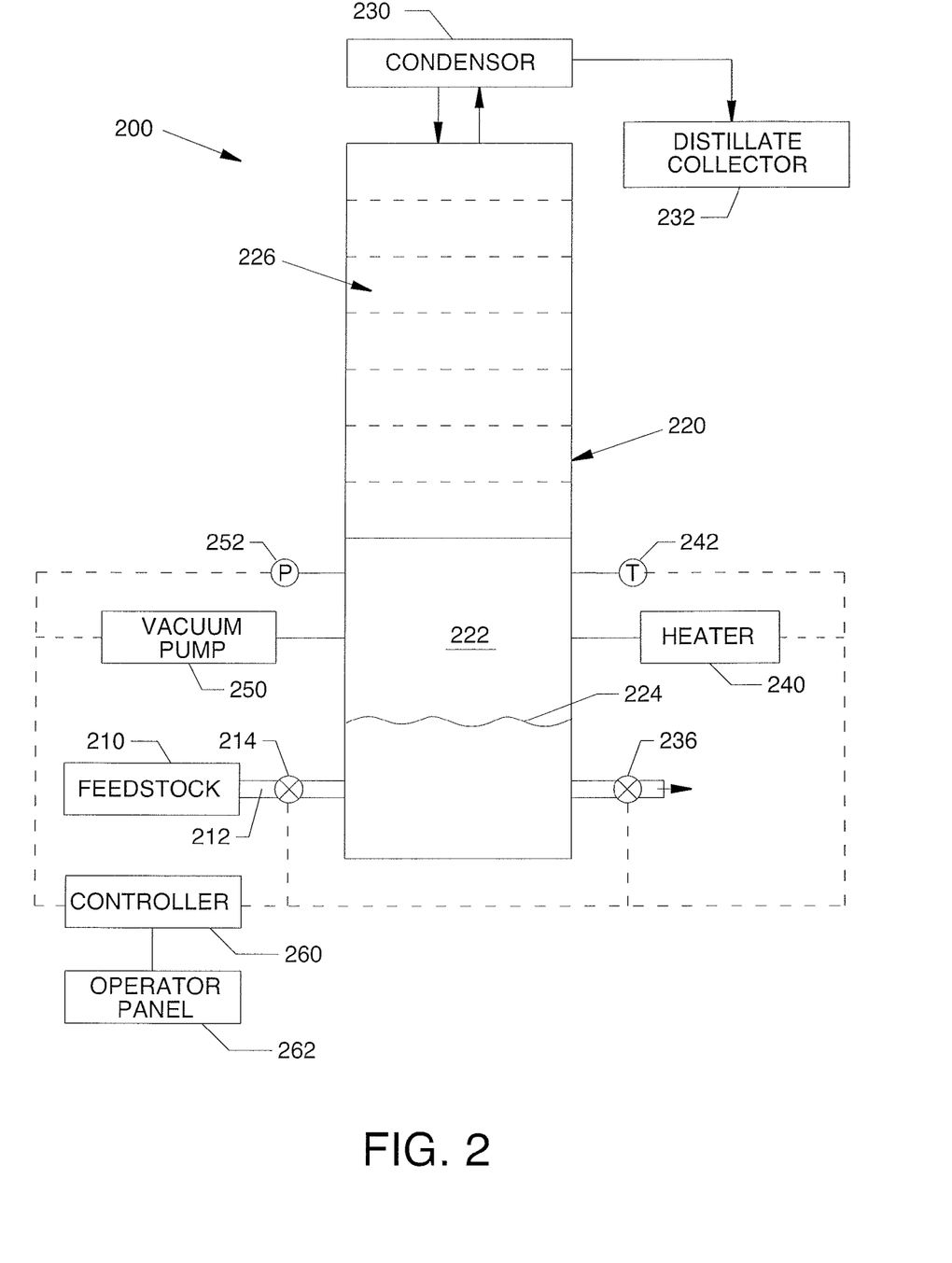
FIG. 2 is a schematic illustration of a system for separating levulinic acid from a glucosamine-containing feedstock in accordance with an embodiment of the invention.

FIG. 2 is a schematic diagram of a levulinic acid separation system 200 in accordance with an embodiment of the disclosure. The levulinic acid separation system 200 of FIG. 2 generally includes a feedstock supply 210, a distillation unit 220, a heater 240, a vacuum pump 250, and a controller 260.

In one embodiment, the feedstock supply 210 may comprise a storage tank configured to receive a quantity of a glucosamine-containing feedstock such as the glucosamine-containing liquor 160 described above. In another embodiment, the feedstock supply 210 may comprise a fluid conduit that communicates the glucosamine-containing liquor 160 from the glucosamine extraction step 150 of the method 100 described above.

Feedstock from the feedstock supply 210 may be delivered to the distillation unit via a fluid conduit 212. The rate of delivery of feedstock from the supply 210 to the distillation unit 220 may be regulated by controlling an inlet valve 214.

The distillation unit 220 has an internal chamber 222 configured to receive the glucosamine-containing feedstock from the feedstock supply 210 and retain a portion of this feedstock as it is subjected to distillation as outlined below. Any of a variety of distillation configurations known in the art may be used for the distillation unit 220. In the illustrated embodiment, the distillation unit 220 comprises a simple vessel formed of a material selected to withstand the chemical, temperature, and pressure conditions of intended operation and sized to receive a suitable quantity of a liquid 224. The distillation unit 220 of FIG. 2 also includes a fractionating column 226 in fluid communication with the internal chamber 222 and a condenser 230 in fluid communication with the fractionating column 226; distillate that condenses in the condenser may be collected in a distillate collector 232. Other embodiments may eliminate one or both of the fractionating column 226 and the condenser 230. In another embodiment, the distillation unit 200 comprises a wiped film evaporator (not shown), such as those available from CHEM Group, Inc, of Evansville, Ind., US. The distillation unit 220 may also include an outlet valve 236 for selectively discharging a residual portion of the contents of the chamber 222, such as at the end of a batch distillation process.

The heater 240 is adapted to selectively heat the liquid 224 in the distillation unit 220. A temperature sensor 242 may be used to monitor the temperature at one or more locations within the chamber 222 or at other locations in the distillation unit, e.g., in the condenser 230. The vacuum pump 250 is in fluid communication with the internal chamber 222 of the distillation unit 220 and may be used to control the pressure in the distillation unit 220. A pressure sensor 252 may be used to monitor the pressure in the chamber 222 or at other locations in the distillation unit.

The controller 260 is operatively coupled to the heater 240, the temperature sensor 242, the vacuum pump 250, the pressure sensor 252, the inlet valve 214, and the outlet valve 236, as suggested by dashed lines in FIG. 2. The controller may communicate with these other components via a direct physical link, through a computer network or other network, or wirelessly. The controller 260 can include a programmable logic controller (PLC), a distributed control system (DCS), a to system logic controller (SLC), a personal computer, and/or other suitable logic processor. The controller 260 can include a computer-readable medium containing instructions for controlling the operation of the levulinic acid separation system 200, as described in more detail below with reference to FIG. 3. In the illustrated embodiment, the controller 260 includes an optional operator panel 262 for providing is process information to an operator and/or receiving input from the operator. In other embodiments, the operator panel 262 can be omitted.

Methods of Separating Levulinic Acid

For ease of understanding, methods of producing a levulinic acid product are described below with reference to the system 200 of FIG. 2. Those skilled in the art will recognize, however, that aspects of such methods can be carried out in other systems.

Figure 3:
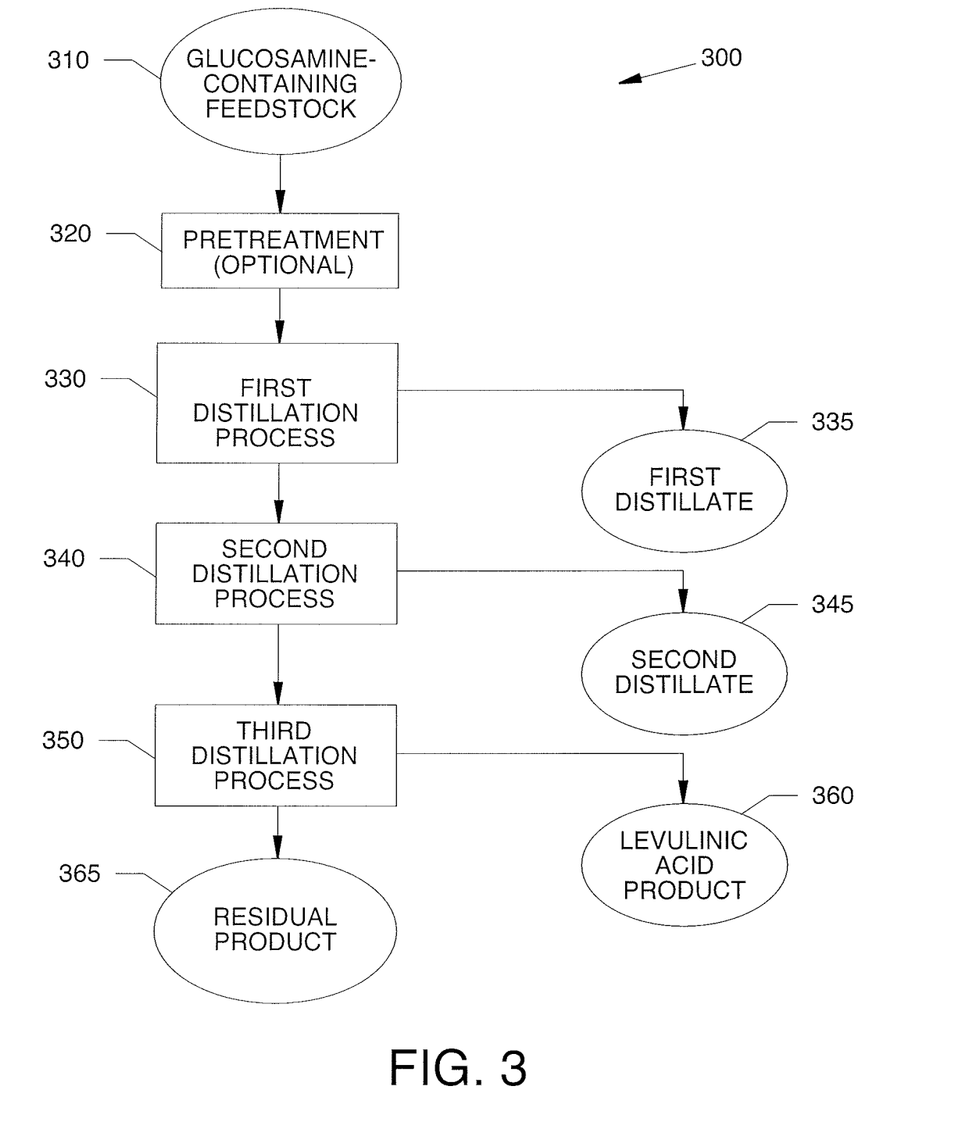
FIG. 3 is a flow diagram schematically illustrating a process in accordance with a further embodiment of the invention.

FIG. 3 is a flow diagram schematically illustrating one useful method 300 for separating levulinic acid from a glucosamine-containing feedstock 310. This method 300 is well-suited to process the liquor 160 described above as the feedstock 310, but may be used with other feedstocks 310 that include both glucosamine and levulinic acid. For example, one useful feedstock 310 includes more than 15 wt % (e.g., 20-35 wt %) levulinic acid, more than 3 wt % (e.g., 4-8 wt %) glucosamine, and more than 0.25 wt % (e.g., 0.5-3 wt %) acetic acid. In one particular embodiment in which the liquor 160 was produced using hydrochloric acid in the acid treatment step 130, such a feedstock also includes more than 5 wt % (e.g., 7-10 wt %) hydrochloric acid. As noted below, the presence of the glucosamine and hydrochloric acid can present some unexpected difficulties in yielding a commercially suitable levulinic acid product from such a liquor 160.

In accordance with the method 300, the feedstock 310 may be pretreated in a pretreatment step 320. The nature and desirability of such an optional pretreatment will depend on the qualities of the feedstock 310. For some lower-quality feedstock sources, it may be desirable to filter or otherwise separate excess solids from the feedstock 310 or to chemically treat the feedstock 310 to reduce the impact of certain impurities. If the liquor 160 produced in the method 100 of FIG. 1 is used as the feedstock 310 in the separation method 300, it is anticipated that the pretreatment 320 can be omitted.

The feedstock 310 (or pretreated feedstock from pretreatment 320, as the to case may be) is delivered to the distillation unit 220 for distillation in a first distillation process 330. In one embodiment, this is done in a batch operation, with a fixed or variable quantity of feedstock 310 being delivered through the conduit 212, after which the valve 214 is closed and the feedstock 310 is treated in the method 300; when the method 300 is completed, a fresh charge of feedstock 310 may be delivered to the distillation unit 220 for treatment.

In a first distillation process 330, the controller 260 monitors the temperature sensor 242 and the pressure sensor 252 and controls the heater 240 and vacuum pump 250 to achieve and maintain a first distillation temperature and a first distillation pressure in the chamber 222. The first distillation temperature is no greater than, and is preferably less than, 100° C., such as 95° C. or less. In one useful embodiment, the first distillation temperature is between 60° C. and 95° C., e.g., 65-90° C. or 75-85° C. This may be the temperature of the liquid 224 in the chamber, for example. In one implementation, a temperature of the vapor in the condenser 230 is maintained during the majority of the first distillation time at a temperature of 30-60° C. to promote condensation of the higher boiling point compounds. (As noted below, this temperature may drop as the end of the first distillation process approaches as the first distillate is removed.)

The first distillation process 330 is conducted at less than atmospheric pressure, with a first distillation pressure of less than 500 torr, e.g., no greater than 300 torr. Lower first distillation pressures, e.g., no greater than 100 torr or no greater than 50 torr, can reduce the first distillation time necessary to achieve the desired degree of separation in the first distillation process. In one useful embodiment, the first distillation pressure is between 5 torr and 50 torr, such as 10-50 torr, 10-30 torr, or 10-20 torr.

The first distillation process 330 is continued for a first distillation time, which will vary somewhat depending on the nature of the feedstock 310 and the selected operating temperatures and pressures. In one useful embodiment, the feedstock 310 includes hydrochloric acid and a substantial majority of that hydrochloric acid is removed in the first distillation. In one embodiment, the condenser 330 may be operated by delivering a relatively constant flow of a cooling medium and the first distillation process may continue until a temperature of the gas in the condenser 330 decreases, e.g., 15-25° C., from a relatively steady equilibrium distillation temperature. This is an indication that a substantial majority of the volatiles driven off at the first distillation temperature and pressure have been removed.

In one useful embodiment, the first distillation time is at least 10 minutes, preferably at least 15 minutes. The maximum length of time will vary somewhat with the first distillation temperature. At a first distillation temperature of about 100° C., the first distillation time should be no longer than 25 minutes, preferably no greater than 15 minutes; continuing longer than 25 minutes can promote undesirable reactions between components of the feedstock that may reduce the yield and/or purity of levulinic acid in the levulinic acid product 360 (discussed below). At a temperature of 80° C., for example, the first distillation time can be much longer, such as 5 hours or longer, though continuing distillation at 80° C. for longer than 3 hours is not expected to be commercially justified.

In one useful implementation, the first distillation time is between 15 and 300 minutes, e.g., 15-180 minutes. At a first distillation temperature of 70-90° C., a first distillation time of 30-120 minutes, e.g., 45-100 minutes, is expected to work well.

In one useful embodiment, the first distillation temperature is 75-85° C., the first distillation pressure is 10-30 torr, and the first distillation time is 60-90 minutes.

Generally, distillation would proceed more quickly if the first distillation temperature was increased and/or the first distillation pressure was decreased. Elevated temperatures, however, are believed to have a substantial deleterious impact on the quality and/or yield of the levulinic acid product 360 by promoting side reactions or decompositions of one or more components in the first product fraction.

The glucosamine-containing liquor 160 produced in the method 100 of FIG. 1 can become rather viscous as water is removed. As noted above, one exemplary fungal biomass treatment method 100 employs hydrochloric acid in the acid treatment step 130 and the glucosamine-containing liquor 160 includes 5 wt % or more hydrochloric acid. Increasing viscosity makes it more difficult to efficiently and effectively remove such hydrochloric acid, which must bubble through the thick fluid. Hydrochloric acid that remains during the later, higher-temperature stages of the method 300 can react with other components of the liquor 160 to generate byproducts that contaminate the levulinic acid product 360. Selecting the first distillation to temperature and first distillation pressure to remove a substantial majority of the free hydrochloric acid initially present in the liquor 160 while some of the water remains can yield a better levulinic acid product 360.

As distillation proceeds in the first distillation process 330, more volatile components of the feedstock 310 will be driven off and condensed as a first distillate 335 in the distillate collector 232, leaving a first product fraction. The composition of the first distillate 335 will depend in part on the nature of the feedstock and the operating conditions of the first distillation process. In one embodiment using the glucosamine-containing liquor 160 from hydrolysis of a fungal biomass as discussed in FIG. 1, the first distillate may include hydrochloric acid, acetic acid, and some water, but it will be relatively poor in levulinic acid as compared to the feedstock 310. For example, the first distillate 335 may include less than 1 wt %, preferably less than 0.5 wt %, levulinic acid.

As the levulinic acid-poor first distillate 335 is removed in the first distillation process 320, the weight percent of levulinic acid in the product retained in the distillation unit 220 will increase. As a consequence, the first product fraction will have a higher levulinic acid content than that of the feedstock 310.

This first product fraction may be treated in a second distillation process 340 at a second distillation temperature and second distillation pressure for a second distillation time. The first product fraction can be moved to a new distillation unit (not shown) for the second distillation process, which may promote a more continuous operation. If the levulinic acid separation method 300 is done as a batch operation, though, the first product fraction may remain in the same distillation unit 220 and the temperature and pressure may be adjusted as necessary to move from the first distillation temperature and pressure to the second distillation temperature and pressure.

The second distillation temperature is higher, preferably at least 10° C. higher, e.g., 10-30° C. or 15-25° C. higher, than the first distillation temperature. In a batch implementation of the separation process 300, the controller 260 can control the heater 240 to increase the temperature in the distillation unit 220. The second distillation temperature is no greater than 115° C., preferably no greater than 110° C. In one useful embodiment, the second distillation temperature is between 80° C. and 110° C., e.g., 90-110° C. or 95-105° C.

The second distillation pressure may differ from the first distillation pressure, but these two pressures may be the same. The second distillation pressure may be less than 500 torr, e.g., no greater than 300 torr. Lower second distillation pressures, e.g., no greater than 100 torr or no greater than 50 torr, can reduce the second distillation time. In one useful embodiment, the second distillation pressure is between 5 torr and 50 torr, such as 10-50 torr, 10-30 torr, or 10-20 torr.

The second distillation time will vary somewhat depending on the composition of the first product fraction left after the first distillation process 330. In one embodiment, the second distillation continues until a significant majority of the water is removed. For example, at least 95 wt %, preferably at least 98 wt %, e.g., 99 wt % or more, of the water in the initial feedstock 310 is removed by the end of the second distillation process 340. In one preferred approach, the water content in the second product fraction that remains at the end of the second distillation process is no greater than 2 wt %, preferably no greater than 1 wt %, e.g., 0.5 wt % or less.

As noted above, removing water from the liquor 160 produced in the method 100 will appreciably increase viscosity of the liquid 224 in the distillation unit 220. This will make it more difficult to remove the levulinic acid in the later stages of the process. However, the liquor 160 in one embodiment includes glucosamine hydrochloride, which may break down into glucosamine and hydrochloric acid in the presence of water. Removing a substantial majority of the water in the second distillation process 340 will limit the amount of free hydrochloric acid that is present in the higher-temperature third distillation process 350 described below. This, in turn, will improve the quality and/or yield of levulinic acid in the method 300 by reducing the side reactions that hydrochloric acid can promote.

In one useful embodiment, the second distillation time is at least 3 minutes, preferably at least 5 minutes. The maximum length of time will vary somewhat with the second distillation temperature and the efficacy of the first distillation process 330. At a second distillation temperature of about 110° C., the second distillation time should be no longer than 30 minutes, preferably no longer than 15 minutes; continuing longer than 30 minutes can promote undesirable reactions between components of the feedstock that may reduce the yield and/or purity of levulinic acid in the levulinic acid product 360.

In one useful implementation, the second distillation time is between 3 and 30 minutes, e.g., 5-25 minutes. At a second distillation temperature of 95-105° C. a first distillation time of 10-20 minutes, e.g., 10-15 minutes, is expected to work well.

The second distillation process 340 will produce a second distillate 345 that may be collected in the same distillation collector 232 as the first distillate 335 or in a second collector 232 (not shown) to keep the two distillates separate for treatment, disposal, or reuse appropriate to each. The example, hydrochloric acid in the first distillate 335 may be recycled for use in the acid treatment step 130 of FIG. 1.

This second distillate 345 may include water and residual amounts of hydrochloric acid, for example, but it will be relatively poor in levulinic acid as compared to the first product fraction. For example, the second distillate 345 may include less than 1 wt %, preferably less than 0.5 wt %, levulinic acid. Removing the second distillate 345 will leave a second product fraction in the distillation unit 220 with a levulinic acid concentration higher than that of the first product fraction.

The second product fraction is treated in a third distillation process 350 at a third distillation temperature and third distillation pressure for a third distillation time. The second product fraction can be moved to a new distillation unit (not shown) for the third distillation process or the second product fraction may remain in the same distillation unit 220 and the temperature and pressure may be adjusted as necessary to move from the second distillation temperature and pressure to the third distillation temperature and pressure.

The third distillation temperature is higher, preferably at least 10° C. higher, e.g., 10-50° C. or 15-25° C., than the first distillation temperature. As in transitioning from the first 330 to the second distillation process 340, transitioning from the second to the third distillation process 350 in a batch process may involve controlling the heater 240 to increase the temperature in the distillation unit 220. The third distillation temperature is no greater than 150° C., preferably no greater than 145° C. Higher temperatures can significantly degrade the quality and/or yield of the levulinic acid product 360. In one useful embodiment, the third distillation temperature is between 120° C. and 150° C., e.g., 125-140° C. or 130-140° C. If so desired, the temperature of the vapor in the condenser 330 during a majority of the third distillation time may be 90-120° C., e.g., 100-110° C.; this temperature will tend to decrease as the end of the third distillation process 350 approaches.

The third distillation pressure may be the same as the second distillation pressure. The third distillation pressure may be less than 500 torr, e.g., no greater than 300 torr. Lower third distillation pressures, e.g., no greater than 100 torr or no greater than 50 torr, can be more effective, with a third distillation pressure between 5 torr and 50 torr, such as 10-50 torr, 10-30 torr, or 10-20 torr, being expected to work well for many applications.

The third distillation time will vary somewhat depending on the composition of the second product fraction and the third distillation temperature. If so desired, the third distillation process 350 can continue until the temperature of the vapor in the condenser 330 decreases, e.g., 15-25° C., from a relatively steady equilibrium temperature. This is an indication that a substantial majority of the levulinic acid has been removed.

In one useful implementation, the third distillation time is between 30 and 300 minutes, e.g., 60-180 minutes. At a third distillation temperature of 125-140° C. a first distillation time of 60-120 minutes, e.g., 90-120 minutes, is expected to work well. In one useful embodiment, the third distillation temperature is 130-140° C., the third distillation pressure is 10-30 time and the third distillation time is 90-120 minutes.

The following table provides distillation temperatures, pressures, and times, in accordance with one useful implementation of the method 300:

| First Distillation Temperature | 65-90° C., e.g., 75-85° C. | First Distillation Pressure | <50 torr, e.g., 10-30 torr | First Distillation Time | 30-180 min., e.g., 60-90 min. |
|---|---|---|---|---|---|
| Second Distillation Temperature | 90-110° C., e.g., 95-105° C. | Second Distillation Pressure | <50 torr, e.g., 10-30 torr | Second Distillation Time | <30 min., e.g., 10-15 min. |
| Third Distillation Temperature | 125-140° C., e.g., 130-140° C. | Third Distillation Pressure | <50 torr, e.g., 10-30 torr | Third Distillation Time | 60-180 min., e.g., 90-120 min. |

The third distillation process yields a levulinic acid product 360 as the distillate and a residual product 365 that may remain in the distillation unit 220. The residual product 365 may be removed from the distillation unit 220 by opening the outlet valve 236.

The nature of the residual product 365 will depend in part on the nature of the initial feedstock 310. If the liquor 160 of method 100 is used as the feedstock 310, the residual product 365 commonly will be a hard, dark residue that may adhere to the walls of the distillation unit 230. Adding acetone and water is expected to help remove the residue. It may be helpful to heat the residual product to a higher temperature, e.g., about 170° C. after completion of the third distillation process 350; doing so is expected to ease removal of the residue from the distillation unit 220.

The residual product 365 produced from the glucosamine-containing liquor 160 may include varying amounts of one or more of glucosamine, glucosamine degradates that may be produced by chemical reaction with and/or thermal is breakdown of glucosamine in the liquor 160, and other complex organic materials that may be present in the liquor 160. In one implementation, elemental analysis (via ICP-AES as noted in the example below) of the residual product 365 has shown that it has relatively high nitrogen and chlorine contents. For example, the nitrogen may be at least 2%, e.g., 2-10% or 3-6%, on an elemental basis of the residual product. Chlorine in some implementations may be similar, with a chlorine content of at least 3%, e.g., 3-10%, on an elemental basis of the residual product. If not carefully managed, nitrogen and/or chlorine might cause undesirable reactions that could adversely impact the quality of the levulinic acid product 360. Such relatively high levels of nitrogen and chlorine in the residual product 365 suggest that embodiments of the invention effectively manage the treatment process to limit their reaction products in the levulinic acid product 360.

The levulinic acid product 360 desirably includes at least 60 wt %, e.g., at least 80 wt %, levulinic acid. More desirably, the levulinic acid content of the levulinic acid product is 85 wt % or more, e.g., 85-95 wt %. The levulinic acid product may also include lesser amounts of minor components such as water. Even under the conditions of the method 300 discussed above, the nitrogen and chlorine contents of the levulinic acid product may be higher than those typically seen in levulinic acid produced from more conventional sources such as sugars or cellulosic materials.

In one adaptation of the method 300, the levulinic acid product 360 recovered as the distillate in the third distillation process is subjected to a further purification process (not shown). The glucosamine-containing feedstock 310 presents some significant processing difficulties not encountered in producing levulinic acid from other known feedstocks. The levulinic acid product 360 produced in the disclosed method 300 has relatively little glucosamine or other problematic components, though, and may be purified in other conventional processes. In one embodiment, this further process may comprise a more conventional vacuum distillation process such as that used to separate levulinic acid from hydrolyzed sugars or the like. In another embodiment, the further purification process may include solvent extraction in addition to or instead of further distillation.

Others have proposed distilling levulinic acid from reaction products that do not include glucosamine, such as that produced by treating starch or cellulose with sulfuric acid. Such reaction products tend to have low concentrations of nitrogen and chlorine. It has been found that conventional distillation of a glucosamine-containing feedstock 310, e.g., the glucosamine-containing liquor 160 of FIG. 1, can significantly degrade the purity and/or yield of levulinic acid. For example, the levulinic acid can be undesirably dark, have an undesirable odor, and/or have undesirable impurities that adversely impact the commercial value of the product.

The first and second distillation processes 330 and 340 may remove a substantial majority of free hydrochloric acid present in the initial feedstock 310, limiting adverse impact on the quality of the levulinic acid product from the hydrochloric acid. Conducting the distillation in two stages under the conditions described above will also limit undesirable reactions between or breakdown of components of the initial liquor 160 that have been found to have deleterious consequences for the levulinic acid product 360.

Surprisingly, it has been found that the quality and/or yield of the levulinic acid product 360 can still be commercially unacceptable if the conditions of the third distillation process are not carefully selected, though. If hydrochloric acid is used in the acid treatment step 130 of FIG. 1, the glucosamine in the liquor 160 may include a significant fraction of glucosamine hydrochloride. It appears that levulinic acid may react with glucosamine or other components of the liquor 160 at temperatures over 150°. Without being bound by theory, we have speculated that temperatures in excess of 150° C. also promote degradation of the glucosamine hydrochloride to free chlorine that reacts with other components of the second product fraction. These reaction products may be as volatile as or more volatile than the levulinic acid under the conditions of the third distillation process 350, so they will collect in the levulinic acid product. Since these reaction products were not initially present in the second to product fraction, they could not be removed in the first and second distillation processes 330 and 340.

EXAMPLES

Aspects of certain methods in accordance with aspects of the invention are illustrated in the following examples. In these examples, the follow were employed:

Equipment: Glassware, Heating plate, Heating mantle

Chemicals: 1) Glucosamine-containing liquor 160 having an initial levulinic acid content of about 27 wt % that was derived from hydrolysis of a chitin-containing fungal biomass with hydrochloric acid as described above in connection with method 100. 2) Commercially available levulinic acid from Sigma-Aldrich Co. 3) Commercially available levulinic acid from Aceto Corp.

Chromatographic Analysis: Liquid chromatography was conducted using a Shimadzu HPLC system with a mobile phase of 0.01N $H_2SO_4$, a column temperature of 60° C., an injection volume of 10.0 μL, and a column flow rate of 0.4 mL/minute.

Elemental Analysis: a Spectra brand inductively coupled plasma atomic emission spectrophotometer (ICP-AES).

Example 1

Small-Scale Distillation

A 49.6 g sample of the glucosamine-containing liquor 160 was distilled in a 300 mL flask equipped with a shortcut distillation head. Usually about 50%-55% of the mother liquor was removed as water and acids (acetic acid, formic acid. HMF and HCl) at an oil bath temperature of 65-70° C. under 15-25 torr vacuum. About 27 g (55%) of low boiling point liquid was collected in the receiver; levulinic acid and a black-brown solid residue remained in the distillation flask. 13.5 g of a levulinic acid product was then distilled at an oil bath temperature of 135 and a distillation head temperature of 91° C. under 10-15 mmHg vacuum. The levulinic acid product was light yellow when it was collected in the receiver. However, the color became darker with time and eventually turned brown. The recovery yield of levulinic acid was around 47%, which has been found to vary with different quality of the liquor 160. The purity of levulinic acid was 93.4% by HPLC. A dark brown char remained in the distillation flask.

The 47% recovery of levulinic acid is believed likely attributable to reactions with glucosamine and other impurities in the liquor 160 at high temperature. Pure levulinic acid (Sigma-Aldrich) was heated at 160° C. No solid was generated, indicating that levulinic acid itself is thermally stable at high temperature. Pure levulinic acid was also mixed with pure glucosamine followed by refluxing. No significant loss of levulinic acid was found. These experiments suggest that the reduced yield is related to side reactions of levulinic acid at high temperature with impurities in the liquor 160 that are not commonly present when producing levulinic acid from more conventional materials.

The levulinic acid product from the initial distillation was distilled again. The resultant levulinic acid was 98-99% pure with light yellow color and a relatively low (454 ppm) chlorine content.

This demonstrates that a levulinic acid separation method 300 in one of the embodiments outlined above can produce a high-quality levulinic acid, which can be sold as a coproduct. In addition, separation of the hydrochloric acid in the first distillate facilitates recycling of hydrochloric acid into the fungal biomass treatment method 100, potentially reducing the net acid consumption in that method 100.

Example 2

Larger-Scale Distillation

A 791 g sample of the glucosamine-containing liquor 160 was added to a 3000 mL round bottom flask equipped with a distillation head and thermometer. Water was distilled from the first product fraction under 10-15 torr vacuum. Compared to the small-scale levulinic acid distillation of Example 1, temperature control in this larger-scale distillation in this example was more difficult and seemed to require a higher temperature to remove water and volatile acids. The thermometer in the distillation head during the second distillation process showed a temperature of 91° C.

The purity of levulinic acid was 80% (water was a primary impurity) and the yield was 34%. The low yield was caused by higher distillation temperature at which more solid char was formed. When the distillation temperature was increased to 170° C. (mantle temperature), the solid black char became loose and was easy to remove from the distillation flask. However, if the temperature was kept at 140-150° C., the char in the flask became very hard. A mixture of acetone and water can gradually dissolve the brown char.

To remove the water from the levulinic acid, a second distillation was carried out and 99% purity levulinic acid was obtained. When the receiver of levulinic acid was cooled by dry ice, levulinic acid was crystallized and stayed in solid form at room temperature. Levulinic acid with high purity more likely tends to crystallize. When the crystallized levulinic acid was heated, it became a liquid, staying in liquid form at room temperature.

CONCLUSION

The glucosamine-containing liquor 160 produced in the fungal biomass treatment method 100 using hydrochloric acid described above is generally viewed as an undesirable waste stream. Embodiments of the invention produce a surprisingly high quality, valuable levulinic acid product from such waste.

Prior attempts to separate levulinic acid from this waste stream in a commercially viable manner were frustrated by complex problems posed by the presence of hydrochloric acid and glucosamine hydrochloride that were neither predicted nor solved by others in the field. Removing a substantial fraction of hydrochloric acid in the first distillation process 320 at conditions to control water loss has been useful. Even after such acid removal, glucosamine hydrochloride in the liquor 160 appears to break down in the presence of water at higher temperatures into glucosamine and hydrochloric acid, which can adversely impact the levulinic acid product 360. The second distillation process 340 in embodiments of the invention limits that breakdown and the unexpected difficulties it poses. Furthermore, the third distillation process 350 has been found to limit volatiles that, we have theorized, may be produced by reaction with chlorine generated from glucosamine hydrochloride. This process 350, in turn, further enhances the quality of the levulinic acid product 360.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can also be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A method for producing levulinic acid, comprising:
    forming a glucosamine-containing feedstock comprising levulinic acid and at least 0.1 wt % glucosamine by
        providing a chitin-containing fungal biomass,
        treating the chitin-containing fungal biomass with an acid having a concentration from 5 to 25 weight percent under reflux conditions to provide a glucosamine composition, and
        extracting the glucosamine composition to provide crystallized glucosamine and a supernatant, wherein the supernatant is the glucosamine-containing feedstock;
    distilling the glucosamine-containing feedstock in a first distillation at a first distillation temperature that is no greater than 110° C. to yield a first product fraction and a first distillate fraction, and wherein the levulinic acid concentration of the first product fraction is higher than the levulinic acid concentration of the glucosamine-containing feedstock; and
    thereafter, distilling the first product fraction in a second distillation at a second distillation temperature that is between 110° C. and 150° C. to yield a levulinic acid product and a residual product, the levulinic acid product comprising at least 60 wt % levulinic acid.

2. A method for producing levulinic acid, comprising:
    distilling a glucosamine-containing feedstock comprising at least 15 percent by weight (wt %) levulinic acid, water, hydrochloric acid and at least 0.5 wt % glucosamine in a first distillation at a first distillation temperature that is no greater than 100° C. and at a first pressure that is no greater than 300 torr to yield a first product fraction and a first distillate fraction, wherein the levulinic acid concentration of the first product fraction is higher than the levulinic acid concentration of the glucosamine-containing feedstock and the hydrochloric acid concentration of the first product fraction is lower than the hydrochloric acid concentration of the glucosamine-containing feedstock;
    thereafter, distilling the first product fraction in a second distillation at a second distillation temperature that is higher than the first distillation temperature, but is no greater than 110° C., and at a second pressure that is no greater than 300 torr to yield a second product fraction and a second distillate fraction, wherein the levulinic acid content of the second product fraction is higher than the levulinic acid concentration of the first product fraction and the water content of the second product fraction is lower than the water content of the first product fraction; and thereafter, distilling the second product fraction in a third distillation at a third distillation temperature that is between 110° C. and 150° C. at a third pressure that is no greater than 300 torr to yield a levulinic acid product and a residual product, the levulinic acid product comprising at least 80 wt % levulinic acid.

3. The method of claim 2 wherein the glucosamine-containing feedstock comprises at least 3 wt % glucosamine.

4. The method of claim 2 wherein the glucosamine-containing feedstock comprises glucosamine hydrochloride.

5. The method of claim 2 wherein the residual product comprises glucosamine, at least 3% nitrogen on an elemental analysis basis, and at least 3% chlorine on an elemental analysis basis.

6. The method of claim 2 wherein the first treatment temperature is between 70° C. and 90° C. and the first pressure is no greater than 50 torr, the first distillation continuing for a first distillation time of 15-300 minutes.

7. The method of claim 2 wherein the second treatment temperature is between 90° C. and 110° C. and the distilling of the first product fraction takes place at a pressure of no greater than 50 torr, the second distillation continuing for a second distillation time of no greater than 30 minutes.

8. The method of claim 2 wherein the third treatment temperature is between 120° C. and 140° C. and the distilling of the second product fraction takes place at a pressure of no greater than 50 torr, the third distillation continuing for a third distillation time of no greater than 30 minutes.

9. A method for producing levulinic acid, comprising:
forming a glucosamine-containing feedstock comprising levulinic acid, water, at least 5 percent by weight (wt %) hydrochloric acid, and at least 1 wt % glucosamine, at least a portion of which is present as glucosamine hydrochloride, by
providing a chitin-containing fungal biomass,
treating the chitin-containing a fungal biomass with hydrochloric acid under reflux conditions to provide a glucosamine composition, and
extracting the glucosamine composition to provide crystallized glucosamine and a supernatant, wherein the supernatant is the glucosamine-containing feedstock the glucosamine-containing feedstock;
distilling the glucosamine-containing feedstock in a first distillation at a first distillation temperature of 70-90° C. and at a first pressure that is no greater than 500 torr for a first distillation time of 15-300 minutes to yield a first product fraction and a first distillate fraction, wherein the levulinic acid concentration of the first product fraction is higher than the levulinic acid concentration of the glucosamine-containing feedstock;

thereafter, distilling the first product fraction in a second distillation at a second distillation temperature that is higher than the first distillation temperature and is between 90° C. and 100° C., and at a second pressure that is no greater than 50 torr to yield a second product fraction and a second distillate fraction, wherein the levulinic acid content of the second product fraction is higher than the levulinic acid concentration of the first product fraction; and thereafter, distilling the second product fraction in a third distillation at a third distillation temperature that is between 120° C. and 140° C. at a third pressure that is no greater than 50 torr to yield a levulinic acid product and a residual product, the levulinic acid product comprising at least 80 wt % levulinic acid.

10. The method of claim 9, further comprising distilling the levulinic acid product to yield a higher-purity levulinic acid product comprising at least 95 wt % levulinic acid.

11. The method of claim 1 wherein the glucosamine-containing feedstock comprises at least 3 wt % glucosamine.

12. The method of claim 1 wherein the glucosamine-containing feedstock comprises glucosamine hydrochloride.

13. The method of claim 1 wherein the residual product comprises glucosamine, at least 3% nitrogen on an elemental analysis basis, and at least 3% chlorine on an elemental analysis basis.

14. The method of claim 1, further comprising distilling the levulinic acid product to yield a higher-purity levulinic acid product comprising at least 95 wt % levulinic acid.

15. The method of claim 2, further comprising distilling the levulinic acid product to yield a higher-purity levulinic acid product comprising at least 95 wt % levulinic acid.

16. The method of claim 2, further comprising forming the glucosamine-containing feedstock by
providing a chitin-containing fungal biomass;
treating the chitin-containing fungal biomass with an acid having a concentration from 5 to 25 percent under reflux conditions to provide a glucosamine composition; and
extracting the glucosamine composition to provide crystallized glucosamine and a supernatant, wherein the supernatant is the glucosamine-containing feedstock.

17. The method of claim 1, where extracting the glucosamine composition comprises: adding ethanol to the glucosamine composition to provide the crystallized glucosamine; and separating the crystallized glucosamine from the supernatant.

* * * * *